(12) United States Patent
Eason et al.

(10) Patent No.: US 7,025,056 B2
(45) Date of Patent: Apr. 11, 2006

(54) ASSYMETRIC INHALER

(75) Inventors: Stephen William Eason, Norfolk (GB);
Raymond Anthony Edgson,
Hertfordshire (GB); **Quentin John
Harmer, Cambridge (GB); Roger
William Clarke**, Cambridgeshire (GB)

(73) Assignee: Vectura Delivery Devices Limited,
Chippenham (GB)

( * ) Notice: Subject to any disclaimer, the term of this patent is extended or adjusted under 35 U.S.C. 154(b) by 0 days.

(21) Appl. No.: 10/477,054

(22) PCT Filed: May 10, 2002

(86) PCT No.: PCT/EP02/05187

§ 371 (c)(1),
(2), (4) Date: Mar. 31, 2004

(87) PCT Pub. No.: WO02/089881

PCT Pub. Date: Nov. 14, 2002

(65) Prior Publication Data

US 2004/0159321 A1    Aug. 19, 2004

(30) Foreign Application Priority Data

May 10, 2001 (GB) .................................. 0111461
Jul. 13, 2001 (GB) .................................. 0117138
Oct. 12, 2001 (GB) .................................. 0124590

(51) Int. Cl.
*A61M 15/00* (2006.01)

(52) U.S. Cl. ................................... 128/203.15; 604/58
(58) Field of Classification Search ........... 128/203.15, 128/203.12, 203.23, 200.18, 200.22; 604/58
See application file for complete search history.

(56) References Cited

U.S. PATENT DOCUMENTS

| 3,155,573 | A | 11/1964 | Fowler |
| 3,921,637 | A | 11/1975 | Bennie et al. ............... 128/266 |
| 4,452,239 | A * | 6/1984 | Malem ................... 128/200.17 |
| 4,860,740 | A * | 8/1989 | Kirk et al. .............. 128/203.15 |
| 4,919,802 | A | 4/1990 | Katsura |
| 4,945,929 | A | 8/1990 | Egilmex ..................... 131/273 |
| 5,476,093 | A | 12/1995 | Lankinen ................... 128/203 |
| 5,596,982 | A | 1/1997 | Blaha-Schnabel ........... 128/200 |
| 5,632,894 | A | 5/1997 | White et al. |
| 5,687,710 | A | 11/1997 | Ambrosio et al. .......... 128/203 |
| 6,113,078 | A | 9/2000 | Rock ............................ 261/21 |
| 6,203,519 | B1 | 3/2001 | Fagerstrom et al. .......... 604/26 |
| 6,394,085 | B1 * | 5/2002 | Hardy et al. ........... 128/203.15 |
| 6,715,486 | B1 * | 4/2004 | Gieschen et al. ...... 128/203.15 |
| 6,748,947 | B1 * | 6/2004 | Keane et al. .......... 128/203.15 |

FOREIGN PATENT DOCUMENTS

| EP | 0407028 | 5/1990 |
| GB | 2340407 | 2/2000 |
| GB | 2344533 | 6/2000 |

(Continued)

*Primary Examiner*—Mital Patel
(74) *Attorney, Agent, or Firm*—Davidson, Davidson & Kappel, LLC

(57) ABSTRACT

An inhaler for producing an inhalable aerosol of a powdered medicament includes an aerosolizing device in the form of a vortex chamber (1). The vortex chamber (1) has a curved wall (12), a tangential inlet port (3) and an axial exit port (2). The radius R of the vortex chamber (1) decreases with angular extend θ. The reduction in effective cross-sectional area of the vortex chamber accelerates the gas flow between the inlet (3) and the outlet (2) to reduce deposition of the medicament.

43 Claims, 5 Drawing Sheets

FOREIGN PATENT DOCUMENTS

| | | |
|---|---|---|
| GB | 2353222 | 2/2001 |
| WO | 9015635 | 12/1990 |
| WO | 9301891 | 2/1993 |
| WO | 9419041 | 9/1994 |
| WO | 9915217 | 4/1999 |
| WO | 9939761 | 8/1999 |
| WO | 0071192 | 11/2000 |
| WO | 0100262 | 1/2001 |

\* cited by examiner

ASSYMETRIC INHALER

BACKGROUND OF THE INVENTION

The present invention relates to inhalers and in particular inhalers for the delivery of a medicament to the lung, more particularly a medicament in powder form.

In recent times, there has been a growing interest in the systemic delivery of pharmaceutically-active medicaments via the lung. Such a method of delivery is generally more attractive to the patient than methods such as injection, because it does not involve a needle and can be carried out discreetly in public.

For a medicament in a particulate form the provision of an inhalable aerosol requires an inhaler that can produce a repeatable dose of fine particles. In order for the particles of medicament to reach the lung and thus be absorbed into the bloodstream, the particles must have an effective diameter in the range of approximately 1 to 3 microns. The portion of the emitted aerosol within this range of particle size is known as the "fine particle fraction". If the particles are larger than 5 microns they may not be transported by the inhaled airflow deep into the lung, because they are likely to be trapped in the respiratory passages before reaching the deep lung. For example, particles of the order of 10 microns are unlikely to progress further than the trachea and particles of the order of 50 microns tend to deposit on the back of the throat when inhaled. Furthermore, if the particles are less than 1 micron in effective diameter, the particles may not be absorbed in the lung, because they are small enough to be expelled from the lung with the exhaled airflow.

Thus, it will be seen that it is important that a powdered medicament is delivered with an accurately controlled range of particle size in order that it is absorbed effectively in the lung.

In traditional metered dose inhalers (MDIs) it is common for the emitted dose (the amount of medicament that enters the patient's airway) to be around 80 to 90% of the dose ejected from the inhaler. The fine particle fraction may be only around 50% of the emitted dose. However, the variation in the fine particle fraction of known inhalers can be ±20 to 30%. Such variation may be acceptable in the case of asthma drugs and the like, but when the medicament is a more potent drug such as insulin, growth hormone or morphine, this amount of variability in the dosing is unacceptable. The relatively low fine particle fraction also represents a significant wastage of what may be an expensive drug. Furthermore, there may be side effects if the proportion of the emitted dose which is not respired is swallowed.

Thus, it is important for the systemic delivery of medicaments by inhalation that a repeatable dose of fine particles can be produced.

WO 90/15635 describes a device for the pulverisation of particles or agglomerates of a powdered inhalation medicament comprising a rotationally symmetrical vortex chamber with spaced inlet and outlet ports. The inlet port directs air inflow into the vortex chamber substantially parallel to the tangent of the chamber. In one arrangement the chamber has a central outlet port.

WO 01/00262 discloses an inhaler comprising a pump, a drug dosing device and a cyclone, which delivers an aerosol of powdered medicament from the drug dosing device into a chamber when the pump is activated. The aerosol is inhaled by the user through a mouthpiece. The cyclone comprises a cylindrical chamber with an axial outlet and a tangential inlet.

Particles of medicament can be separated by generating shear forces between the particles, for example by providing a substantial velocity gradient across the particles. This may be done, for example, by forcing the powder through a narrow nozzle at high speed or introducing the powder into a turbulent air stream. Alternatively, a cyclone of the type described in WO 01/00262 can be used.

SUMMARY OF THE INVENTION

The present invention, at least in its preferred embodiments, seeks to provide an inhaler which is capable of reliably generating an inhalable aerosol of a powdered medicament with an effective particle size that is sufficiently small for the medicament to be delivered to and absorbed in the lungs of a patient.

Viewed from a first aspect, the invention provides an inhaler for producing an inhalable aerosol of a powdered medicament comprising an aerosolising device in the form of a vortex chamber having an axis and being defined, at least in part, by a wall which forms a curve about the axis, the vortex chamber having a cross-sectional area in a plane bounded by the axis, the plane extending in one direction radially from the axis at a given angular position ($\theta$) about the axis, wherein the vortex chamber has a substantially tangential inlet port and a substantially axial exit port, and said cross-sectional area of the vortex chamber decreases with increasing angular position ($\theta$) in the direction, in use, of gas flow between the inlet port and the exit port.

Thus, according to the invention, the aerosolising device of the inhaler is arranged such that a flow of gas entering the vortex chamber through the inlet port is guided in a rotating path until it leaves the vortex chamber via the exit port. The exit port is generally aligned with the axis of rotation of the gas flow. When a powdered medicament is entrained in the gas flow, shear forces due to the velocity gradient in the boundary layer adjacent the wall of the vortex chamber break up the agglomerated particles of medicament to form an aerosol of fine particles.

The inventors have realised that in a cylindrical vortex chamber, such as that described in WO 01/00262, powder deposits can build up around the periphery of the device. These deposits are undesirable in a re-usable inhaler because they may subsequently become detached and added to a later dose.

By decreasing the effective cross-sectional area of the gas flow path through the vortex chamber, the gas flow is accelerated and deposition of the entrained medicament is thereby reduced. In this way, the velocity of a gas flow of constant mass flow rate increases as the flow moves around the vortex chamber. The increasing velocity reduces the deposition of medicament entrained in the gas flow during its passage through the vortex chamber.

In one arrangement, the distance (R) of the wall from the axis decreases with angular position ($\theta$). Thus, the vortex chamber may be in the form of a spiral or scroll. The distance (R) of the wall from the axis may decrease with angular position ($\theta$) substantially in accordance with the relationship $R=R_{max}\{1-f(\theta)\}$, where $R_{max}$ is a maximum radius, $f(\theta)$ is a function of $\theta$, $0 \leq f(\theta) < 1$ for $0 \leq \theta < 2\pi$ and $df/d\theta \geq 0$ for $0 < \theta < 2\pi$ and $df/d\theta > 0$ for at least some of the range $0 \leq \theta < 2\pi$. In particular, $df/d\theta$ may be greater than zero for substantially the whole range $0 \leq \theta < 2\pi$. In this case the radius of the vortex chamber is constantly decreasing. Preferably, the radius of the vortex chamber decreases linearly, i.e. $df/d\theta$ is constant.

In one embodiment, $f(\theta)$ is substantially given by $f(\theta)=\theta(k/2\pi)$, where k is a constant and $0<k<1$. Generally, $5\%<k<75\%$, preferably $15\%<k<45\%$, most preferably $20\%<k<35\%$. In the preferred embodiment, $k=28.6\%$.

The vortex chamber may be further defined by a base and, optionally, a roof. The distance (H) between the base and the roof may decrease with angular position ($\theta$).

The inventors have realised that in a plain cylindrical vortex chamber, powder deposits build up around the periphery of the device in the manner of a snowdrift. The shape formed by the powder deposits is like a helical ramp but with filleted or curved edges following the airflow. The inventors have found that by modifying the geometry of the vortex chamber so that the base and walls of the vortex chamber substantially follow the pattern of powder deposition, the amount of powder deposited from a dose can be reduced.

Modifying the geometry to follow this arrangement further reduces the deposition by virtue of decreasing the distance between the base and the (flat) top of the vortex chamber with angular extent around the vortex chamber axis. Air going around the periphery of the vortex chamber in this region of decreasing height maintains its velocity more effectively and powder is more likely to remain entrained in the airflow. Furthermore, this airflow is more likely to scour deposited powder from the walls.

The distance between the base and the top of the vortex chamber (H) can decrease with angular extent in a number of ways. In a preferred embodiment, the decrease in height occurs linearly with increasing angular extent. In a further arrangement, the rate of decrease in H can increase with increasing angular extent. Advantageously, for ease of manufacture, the decrease in H or rate of decrease of H can occur in a number of discrete steps.

The distance (H) between the base and the roof may decrease with angular position ($\theta$) substantially in accordance with the relationship $H=H_{max}\{1-g(\theta)\}$, where $H_{max}$ is a maximum height, $g(\theta)$ is a function of $\theta$, $0\leq g(\theta)<1$ for $0\leq\theta<2\pi$ and $dg/d\theta\geq 0$ for $0<\theta<2\pi$ and $dg/d\theta>0$ for at least some of the range $0\leq\theta<2\pi$.

The function $g(\theta)$ may be substantially zero for $0\leq\theta<\theta_1$ where $\theta_1$ is a constant, with $dg/d\theta>0$ for at least some of the range $\theta_1\leq\theta<2\pi$. In this way, the distance between the base and the roof does not start to decrease until after a defined angular position ($\theta_1$). The value of $\theta_1$ may be zero. Suitable values of $\theta_1$ are in the range 0° to 300°, preferably 20° to 180°, most preferably 40° to 80°. In the preferred embodiment, the value of $\theta_1$ is 58°.

The function $g(\theta)$ for the range of values of $\theta_1\leq\theta<\theta_{max}$ may be substantially given by $g(\theta)=j(\theta-\theta_1)/(\theta_{max}-\theta_1)$, where j is a constant and $0<j<1$. Generally, $10\%<j<95\%$, preferably $25\%<j<75\%$, most preferably $40\%<j<60\%$. In the preferred embodiment, $j=50\%$. The value $\theta_{max}$ represents a maximum value of $\theta$, which may take any value up to $2\pi$ radians. The maximum value $\theta_{max}$ may be a function of radial position (r).

The distance (H) between the base and the roof may decrease with radial position (r) relative to the axis. Indeed, in more general terms, the distance (d) between the base and a plane normal to the axis may increase with radial position (r) relative to the axis. The plane should be located on the opposite side of the base to the exit port.

This in itself is believed to be a novel arrangement and thus viewed from a further aspect the invention provides an inhaler for producing an inhalable aerosol of a powdered medicament comprising an aerosolising device in the form of a vortex chamber having an axis and being defined, at least in part, by a wall which forms a curve about the axis, the vortex chamber having a substantially tangential inlet port and a substantially axial exit port, wherein the vortex chamber is further defined by a base, and the distance (d) between the base and a plane which is normal to the axis and is located on the opposite side of the base to the exit port increases with radial position (r) relative to the axis.

The distance (d) between the base and the normal plane may increase with radial position (r) substantially in accordance with the relationship $d=d_{max}\,e(r)$, where $d_{max}$ is a maximum distance, $e(r)$ is a function of r, $0\leq e(r)<1$ for $0\leq r\leq R_{max}$ and $de/dr\geq 0$ for $0\leq r\leq R_{max}$ and $de/dr>0$ for at least some of the range $0\leq r\leq R_{max}$.

The function $e(r)$ may be substantially zero for $0\leq r<r_1$ where $r_1$ is a minimum radius and $de/dr>0$ for at least some of the range $r_1\leq r\leq R_{max}$. The minimum radius, $r_1$, may be a function of angular position, for example in the same manner as the radius R of the chamber. The minimum radius, $r_1$, may alternatively be constant. Generally, the minimum radius, $r_1$, is 5 to 95%, preferably 10 to 80%, most preferably 20 to 60% of the maximum radius $R_{max}$ of the vortex chamber. In the preferred embodiment, the minimum radius, $r_1$, is 40% of the maximum radius $R_{max}$ of the vortex chamber.

The function $e(r)$ for the range of values of $r_1\leq r\leq R_{max}$ may be substantially given by $e(r)=m(r-r_1)/(R_{max}-r_1)$, where m is a constant and $0<m<1$.

In a preferred arrangement, the distance (H) between the base and the roof decreases with radial position and with angular position. For example, the distance (H) between the base and the roof may be given substantially by $H=H_{max}\{1-e(r)\}\times\{1-g(\theta)\}$.

The wall may form a substantially smooth curve. Alternatively, the wall may form a stepped curve, for example for manufacturing ease. Preferably, the interface between the base and the wall is formed by a substantially smooth transition. The roof may be planar. The plane of the roof may be substantially normal to the axis.

The inlet port can be considered as the end portion of an inlet conduit through which a gas flow enters the chamber, in use. Similarly, the exit port can be considered as the beginning portion of an exit conduit through which the gas flow exits the vortex chamber, in use. An axial exit port directs the gas flow out of the vortex chamber in a substantially axial direction or with a substantial component in the axial direction.

The ratio of the maximum diameter of the vortex chamber (calculated as twice the maximum radius $R_{max}$) to the diameter of the exit port can be significant in maximising the fine particle fraction of the medicament aerosol which is expelled from the exit port. It has been found that when the ratio is between 4 and 12 the proportion of particles of the powdered medicament with an effective diameter in the range 1 to 3 microns is maximised. For an enhanced fine particle fraction, the ratio is preferably greater than 5, most preferably greater than 6 and preferably less than 10, most preferably less than 9. In the preferred arrangement, the ratio is 8.

In embodiments of the invention, the maximum radius of the vortex chamber is between 1 and 6 mm. The maximum radius of the vortex chamber is preferably greater than 2 mm, most preferably at least 2.5 mm and preferably less than 4 mm, most preferably less than 3 mm. In the preferred embodiment, the maximum radius of the vortex chamber is 2.8 mm.

In embodiments of the invention, the maximum height ($H_{max}$) of the vortex chamber is between 1 and 8 mm. The maximum height of the vortex chamber is preferably less than 4 mm, most preferably less than 2 mm. In the preferred embodiment, the maximum height of the vortex chamber is 1.6 mm.

In general, the vortex chamber is substantially prismal, i.e. has a constant cross-section in the directions of the axis. However, it is within the scope of the invention for the vortex chamber to take other forms. For example, the vortex chamber may be frustoconical, i.e. may have sides which are not parallel. Where the maximum diameter of the vortex chamber or the diameter of the exit port is not constant along its length, the ratio of the largest diameter of the vortex chamber to the smallest diameter of the exit port should be within the range according to the invention.

In embodiments of the invention, the diameter of the exit port is between 0.5 and 2.5 mm. The diameter of the exit port is preferably greater than 0.6 mm and preferably less than 1.2 mm, most preferably less than 1.0 mm. In the preferred embodiment, the diameter of the exit port is 0.7 mm.

The exit port may comprise a plurality of apertures or passageways. In this case, the diameter of the exit port is considered as the diameter of the smallest circle which circumscribes all of the apertures or passageways which form the exit port.

The inhaler may comprise an exit conduit through which the medicament aerosol passes after leaving the vortex chamber. The exit port may form part of the exit conduit nearest the vortex chamber. If the exit conduit is short, the exit port may form all of the exit conduit.

The exit conduit may be in the form of a tube. The inventors have found, however, that deposition of the aerosolised medicament can occur in a tubular exit conduit, which leads to uncertainty in the dose emitted by the inhaler. Nevertheless, a long exit conduit decreases the plume angle of the medicament aerosol as it exits the conduit and therefore reduces the deposition on the mouthpiece. However, this may increase deposition in the user's throat. Preferably, therefore, the length of the exit conduit or port is short, for example less than the diameter of the exit port. A short exit conduit (or port) increases the plume angle of the medicament aerosol as it exits the conduit (or port) and therefore decreases the speed of the aerosol to reduce deposition in the user's throat.

Thus, the length of the exit port may be less than the diameter of the exit port. In a preferred arrangement, the length of the exit port is less than half the diameter of the exit port.

Where the diameter of the exit port is not constant along its length, the length of the portion of the exit port having the smallest diameter should be less than that diameter.

In general, the exit port may be defined as a passage through a wall of the vortex chamber. In this case, the length of the exit port may depend on the thickness of the wall. The wall, or a portion thereof, may be tapered (or otherwise reduced in thickness) towards the exit port so that the length of the exit port is less than the maximum thickness of the wall. In particular, the perimeter of the exit port may be in the form of a knife-edge, i.e. a region of negligible thickness.

The inlet port may have any suitable cross-section. For example, the inlet port may have a substantially circular cross-section.

In a preferred configuration, the inlet port has an outer wall which defines the maximum extent of the inlet port in the radially outward direction of the vortex chamber. The extent of the outer wall in the axial direction of the vortex chamber is substantially equal to the maximum extent of the inlet port in the axial direction of the vortex chamber. The outer wall may be substantially parallel with the wall of the vortex chamber.

Thus, the inlet port may be configured such that its radially outer wall is parallel to the wall of the vortex chamber along substantially the entire axial length of the inlet. In this way, a gas flow with entrained particles of medicament is able to enter the vortex chamber across the whole inlet port along a line which is parallel to the wall of the vortex chamber. This arrangement assists in maximising the proportion of the entrained particles which enter the boundary layer adjacent the wall of the vortex chamber where the shear forces generated by the vortex are at a maximum. In the boundary layer, the maximised shear forces produce maximum deagglomeration of the particles of medicament.

In a preferred arrangement, the outer wall of the inlet port is provided by the wall of the vortex chamber. In this way, the entrained particles of medicament are able to enter directly the boundary layer of the vortex across the whole inlet port.

The cross-section of the inlet port in accordance with this aspect of the invention may take any suitable form relative to the outer wall. For example, the inlet port may be wedge-shaped or quadrant-shaped. In the preferred arrangement, for reasons of simplicity, the inlet port is rectangular in cross-section.

The inlet port may have a height in the axial direction up to the height of the vortex chamber. The height of the inlet port may be greater than 1 mm and preferably less than 2 mm. In the preferred configuration, the height of the inlet port is 1.6 mm.

The width of the inlet port in the radial direction may be less than 1 mm. Preferably the width of the inlet port is greater than 0.2 mm, more preferably greater than 0.4 mm. The width of the inlet port is preferably less than 0.8 mm, more preferably less than 0.6 mm. In the preferred configuration, the width of the inlet port is 0.5 mm.

Advantageously, the maximum width of the inlet port is substantially equal to the width of the inlet port at the end furthest in the axial direction from the exit port of the vortex chamber. In this way, the particles of medicament entering the vortex chamber through the inlet port are encouraged initially towards the region of the chamber furthest from the exit port where the inlet port is widest. Thus, the residence time of the particles in the vortex chamber is maximised, thereby allowing more time for effective deagglomeration. The width of the inlet port may be constant along its axial extent.

In a preferred arrangement, the bottom surface (base) of the vortex chamber also defines the furthest axial extent of the inlet port. According to this arrangement, the bottom wall of the inlet port is provided by the base of the vortex chamber. It has been found that such a configuration significantly reduces the deposition of medicament in the vortex chamber, in use.

The inhaler may comprise an inlet conduit arranged to supply a gas flow to the inlet port, in use. The gas flow may contain particles of entrained medicament.

The inlet conduit may have a constant cross-sectional area in the tangential direction towards the vortex chamber. Preferably, however, the cross-sectional area of the inlet conduit decreases towards the vortex chamber. Thus, the inlet conduit may taper towards the vortex chamber. In this way, the velocity of a gas flow of constant mass flow rate increases as the flow moves towards the vortex chamber.

The increasing velocity reduces the deposition of medicament entrained in the gas flow during its passage through the inlet conduit.

In embodiments of the invention, the rate of decrease of cross-sectional area with distance of the inlet conduit is between 1% and 30% per millimeter. The rate of decrease is preferably greater than 2% per mm, more preferably greater than 3% per mm and preferably less than 20% per mm, more preferably less than 10% per mm. In the preferred embodiment the rate of decrease is 5% per millimeter.

Preferably, the inlet conduit comprises an outer wall which is substantially tangential to the vortex chamber at the inlet port and an inner wall which converges towards the outer wall in the direction towards the vortex chamber. According to this arrangement, the inner wall guides the incoming gas flow towards the outer wall, such that the gas flow is directed towards the boundary layer of the vortex inside the vortex chamber.

The inlet conduit may be straight, for example the outer wall and the inner wall may be rectilinear. It is within the scope of the invention that only one of the outer wall and the inner wall is rectilinear. In an advantageous embodiment, the inlet conduit is arcuate. This has the advantage that angular momentum is imparted to the incoming gas flow and entrained medicament particles as they pass through the inlet conduit even before they enter the vortex chamber. Thus, the inlet conduit is preferably concavely arcuate relative to the axis of the vortex chamber. The inlet conduit may be arcuate about the axis of the vortex chamber. In this way, the centrifugal force on the incoming gas flow propels the entrained particles of medicament towards the outside edge of the inlet conduit so that the particles enter the vortex chamber adjacent the boundary layer where shear forces are at a maximum.

The curvature of the inlet conduit is preferably sufficient that a tangent to the inner wall at the entrance of the conduit intercepts the outer wall before the end of the conduit. In this way, it is ensured that any particle following a straight path will reach the outer wall of the inlet conduit before entering the vortex chamber.

The arcuate inlet conduit may be any suitable length and have any suitable radius or radii of curvature. In one arrangement, the inlet conduit is in the form of a spiral around the vortex chamber. This arrangement allows a long inlet conduit, for example with only a slight taper, to be provided in a relatively compact way.

The air flow to the inlet port of the vortex chamber may be generated by the user inhaling and drawing air through the exit port. However, this is not preferred, because the flow rate through the vortex chamber is then dependent on the inhalation rate of the user. It has been found that the fine particle fraction of the medicament aerosol can depend on the flow rate through the vortex chamber.

Thus, in preferred embodiments of the invention, the air flow to the vortex chamber is provided by a source of pressurised air. In this way, an air flow of repeatable volume and velocity can be provided to the vortex chamber in order to minimise variations in the composition of the generated aerosol.

For example, the inhaler may be arranged for connection to a compressed air line or other source of pressurised gas. However, this is not preferred as it is desirable for the inhaler to be self-contained. Consequently, the inhaler may comprise a canister of pressurised gas. The canister may comprise a valve for selectively supplying a gas flow to the vortex chamber. The canister may be rechargeable, for example by means of a pump.

Alternatively, the inhaler may comprise a pump for providing an air flow to the vortex chamber. A pump has the advantage that it does not require recharging or replacing in the manner of a gas canister. The pump may be in any suitable form, for example a squeeze bulb, a bellows pump or such like. A preferred type of pump is a piston pump, in particular a spring-powered piston pump. The piston pump may comprise a plunger received in a pump cylinder. The plunger may be arranged to be withdrawn from the pump cylinder to a primed position against the restoring force of a spring. The plunger may be released when required such that the spring forces the plunger into the pump cylinder to generate an air flow.

In general, the air flow from the pump, canister or other source of pressurised gas is supplied to the vortex chamber via a drug entrainment device.

Thus, the inhaler may comprise a drug entrainment device which is arranged to entrain the powdered medicament in an air flow to the inlet port of the vortex chamber. The drug entrainment device may comprise a substantially cylindrical entrainment chamber having a substantially tangential inlet. The entrainment chamber may also comprise a substantially tangential outlet spaced axially from the inlet.

The inhaler may comprise a mouthpiece and the vortex chamber may be arranged to expel the medicament aerosol into the mouthpiece through the exit port. A mouthpiece locates the vortex chamber relative to the user's airway and allows the medicament aerosol to be directed into the airway. Preferably, the inhaler comprises at least one air passage which allows air to be inhaled through the mouthpiece in addition to the medicament aerosol. The provision of such an air passage allows the user to take a full breath even when the volume of the aerosol is relatively small. The additional air breathed in by a user may be beneficial in propelling the aerosol into the user's lungs.

The inhaler may comprise a breath-actuation device which is arranged to actuate the pump, canister or other source of pressurised gas when the user inhales. The mouthpiece may comprise the breath-actuation device.

The terms "axial", "radial" and "tangential" are used herein to define the geometry of the vortex chamber. These terms are best understood by reference to the vortex formed within the vortex chamber in use. Thus, the axial direction is a direction parallel to the axis about which the vortex rotates. The radial direction is a direction outward from the axis about which the vortex rotates. The tangential direction is a direction parallel to the instantaneous direction of motion of a particle in the vortex. Consequently, it is not necessary for the vortex chamber to have a perfectly arcuate cross-section, and the vortex chamber need only be sufficiently curved to form an effective vortex. It is desirable for the perimeter of the vortex chamber to form a smooth curve, as it has been found that an angular perimeter can lead to deposition of the medicament in the vortex chamber. However, manufacturing considerations may mean that the wall of the vortex chamber is formed by a series of connected portions, rather than a continuous curve.

In accordance with another embodiment of the present invention an inhaler is provided for producing an inhalable aerosol of a powdered medicament. The inhaler includes a chamber defined by a top wall, a bottom wall, and a lateral wall, the lateral wall being curved about an axis which intersects the top wall and the bottom wall, the chamber enclosing a cross-sectional area defined by the axis, the top wall, the bottom wall and the lateral wall. The chamber has an inlet port and an outlet port, the inlet port being tangent to the lateral wall, the outlet port being co-axial with the axis, the cross-sectional area decreasing with increasing angular position from the inlet port in a direction of a gas flow through the inlet port.

In accordance with a further embodiment of the present invention an inhaler is provided for producing an inhalable aerosol of a powdered medicament. The inhaler includes a chamber including a wall, a base, an inlet port and an exit port, the chamber having an axis that is co-axial with the exit port and intersects the base, the wall being curved about the base, the inlet port being tangential to the wall. A height between the base and a plane normal to the axis at the exit port decreasing as a radial position from the axis to the inlet port increases.

In accordance with yet a further embodiment of the present invention a method of inhaling an aerosol of a powdered medicament is provided. The method includes: generating an air flow through an inlet port of a chamber; directing the air flow through the chamber, the chamber having an axis and a wall curved about the axis, the air flow rotating about the axis; and directing the air flow through an exit port of the chamber. A direction of the air flow through the inlet port is tangential to the wall, and a direction of the air flow through the exit port is parallel to the axis. A cross-sectional area of the air flow through the chamber is in a plane normal to the air flow and decreases with increasing distance from the inlet port.

BRIEF DESCRIPTION OF THE DRAWINGS

Some embodiments of the invention will now be described by way of example only and with reference to the accompanying drawings, in which.

In the various embodiments of the invention, corresponding components are given corresponding reference numerals.

DETAILED DESCRIPTION

Figure 1:
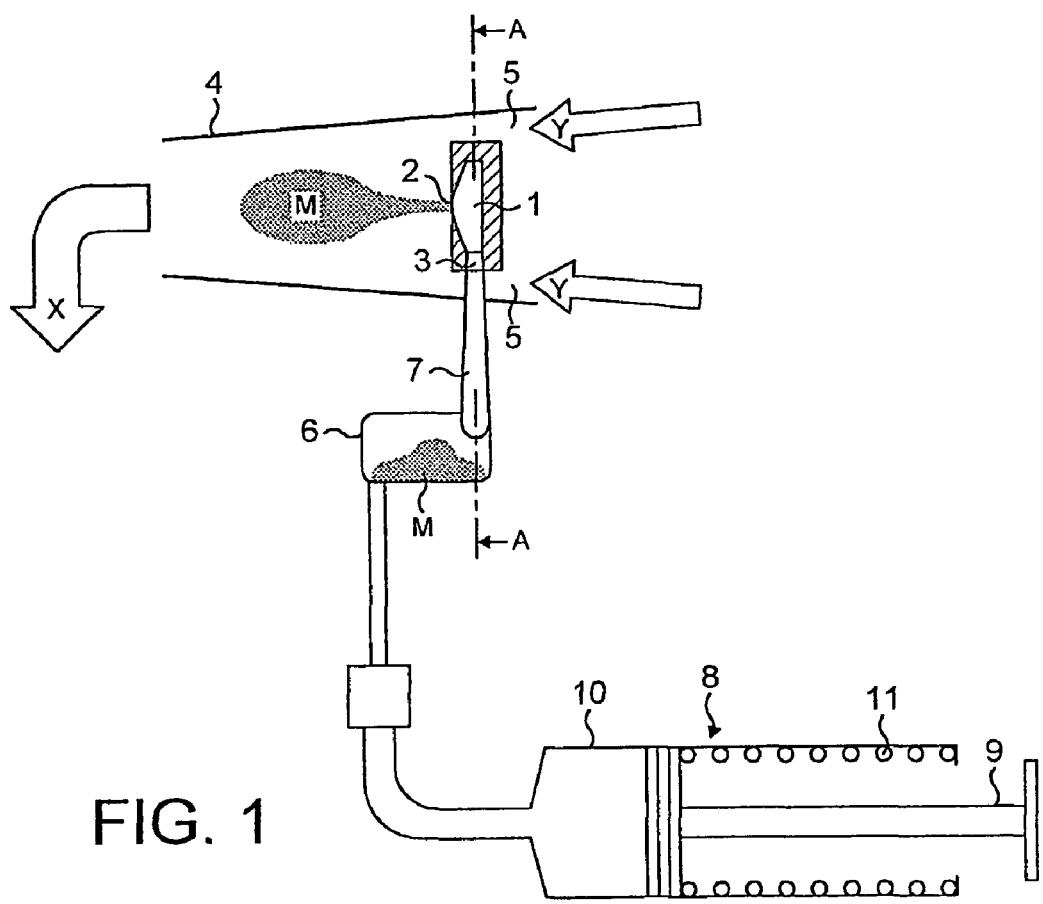
FIG. 1 is a schematic view, partially in section, of an inhaler according to an embodiment of the invention.

FIG. 1 shows schematically a prototype inhaler according to an embodiment of the invention. The inhaler aerosolises a drug in dry powder form for inhalation by the user.

As shown in FIG. 1, the inhaler comprises a vortex chamber (or nozzle) 1 having an exit port 2 and an inlet port 3 for generating an aerosol of medicament M. The vortex chamber 1 is located in a mouthpiece 4 through which the user inhales in use of the inhaler, as indicated by the arrow X. Air passages 5 are defined between the vortex chamber 1 and the mouthpiece 4 so that the user is able to inhale air in addition to the medicament aerosol M, as indicated by arrows Y.

The powdered medicament (or drug) M is provided to the vortex chamber 1 in an air flow from a drug entrainment device 6 via an inlet conduit 7. The drug entrainment device 6 is in the form of a cylindrical chamber with tangential inlet and outlet ports spaced in the axial direction. The drug may be supplied for transfer to the drug entrainment chamber in a foil blister or a standard gelatin capsule, containing 1 to 5 milligrams of powdered drug. The optimum particle size of the drug for delivery to the deep lung is 1 to 3 microns. If necessary an inert excipient, such as lactose, can be added to the drug to increase its bulk and improve its handling properties. Non-limiting examples of formulations with which the inhaler may be used are micronised pure drugs such as sodium cromoglycate, terbutaline sulphate and pure salbutamol sulphate, and spray-dried formulations of drugs such as insulin and paracetamol with a carrier such as hydroxy-ethyl starch.

The air flow to the drug entrainment device 6 is provided by a pump 8, represented in FIG. 1 as a spring-powered piston pump. The pump 8 comprises a plunger 9 received in a pump cylinder 10 and biased into the pump cylinder 10 by a spring 11. The pump 8 is selected to have a capacity of less than 100 ml, preferably less than 50 ml and more preferably between 5 and 25 ml in order that the total size of the inhaler is relatively small. The pump 8 is capable of generating a pressure between 0.5 and 10 bar gauge, preferably less than 5 bar and more preferably less than 2 bar in order that the total size of the inhaler is relatively small. The flow rate through the inhaler is typically 1 to 5 liters per minute and may be adjusted for optimum performance with a particular medicament.

In use of the inhaler, the pump 8 is primed by retracting the plunger 9 against the force of the spring 11. The plunger 9 is retained in the primed position by a breath-actuated mechanism (not shown) until the user inhales. When the user inhales, the plunger 9 is released by the breath-actuated mechanism and the spring 11 forces the plunger 9 in to the pump cylinder 10. In this way, air is forced through the drug entrainment device 6 where the powdered medicament M is entrained in the air flow. The air flow transports the medicament M to the vortex chamber 1, where a rotating vortex of medicament and air is created between the inlet port 3 and the outlet port 2. Rather than passing through the vortex chamber in a continuous manner, the powdered medicament entrained in the airflow enters the vortex chamber in a very short time (less than 0.3 seconds) and a proportion of the powdered medicament sticks to the walls of the vortex chamber. This powder is subsequently aerosolised by the high shear forces present in the boundary layer adjacent to the wall. The action of the vortex deagglomerates the particles of medicament M so that an aerosol M of powdered medicament exits the vortex chamber 1 via the exit port 2. The aerosol is inhaled by the user through the mouthpiece 4.

The vortex chamber 1 can be considered to perform two functions: deagglomeration, the breaking up of clusters of particles into individual, respirable particles; and filtration, preferentially allowing particles below a certain size to escape more easily from the exit port 2. Deagglomeration breaks up cohesive clusters of powdered medicament into respirable particles, and filtration increases the residence time of the clusters in the vortex chamber 1 to allow more time for them to be deagglomerated. Deagglomeration can be achieved by creating high shear forces due to velocity gradients in the airflow in the vortex chamber 1. The velocity gradients are highest in the boundary layer close to the walls of the vortex chamber.

Figure 2:
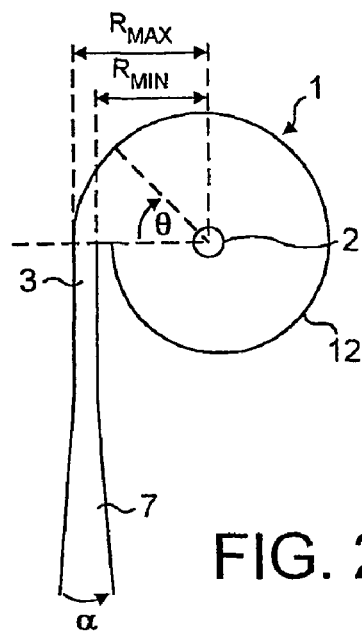
FIG. 2 is a sectional view along line A—A of a detail of the embodiment of FIG. 1.

As shown in more detail in FIG. 2, the wall 12 of the vortex chamber 1 is in the form of a spiral or scroll. The inlet port 3 is substantially tangential to the perimeter of the vortex chamber 1 and the exit port 2 is generally concentric with the axis of the vortex chamber 1. Thus, gas enters the vortex chamber 1 tangentially via the inlet port 3 and exits axially via the exit port 2.

The radius R of the vortex chamber 1 measured from the centre of the exit port 2 decreases smoothly from a maximum radius $R_{max}$ at the inlet port 3 to a minimum radius $R_{min}$. Thus, the radius R at an angle $\theta$ from the position of the inlet port 3 is given by $R=R_{max}(1-\theta k/2\pi)$, where $k=(R_{max}-R_{min})/R_{max}$. The effective radius of the vortex chamber 1 decreases as the air flow and entrained particles of medicament circulate around the chamber 1. In this way, the effective cross-sectional area of the vortex chamber 1 experienced by the air flow decreases, so that the air flow is accelerated and there is reduced deposition of the entrained particles of medicament. In addition, when the flow of air has gone through $2\pi$ radians (360°), the air flow is parallel to the incoming airflow through the inlet port 3, so that there is a reduction in the turbulence caused by the colliding flows.

Between the inlet port 3 and the exit port 2 a vortex is created in which shear forces are generated to deagglomerate the particles of medicament. The length of the exit port 2 is as short as possible to reduce the possibility of deposition of the drug on the walls of the exit port 2. In the embodiment shown, the vortex chamber 1 is machined from acrylic or brass, although a wide range of alternative materials is possible. For manufacturing ease, the radius of the vortex chamber 1 may decrease in steps rather than smoothly.

TABLE 1

Vortex chamber dimensions

| Dimension | | Value |
|---|---|---|
| $R_{max}$ | Maximum radius of chamber | 2.8 mm |
| $R_{min}$ | Minimum radius of chamber | 2.0 mm |
| $H_{max}$ | Maximum height of chamber | 1.6 mm |
| h | Height of conical part of chamber | 0.0 mm |
| $D_e$ | Diameter of exit port | 0.7 mm |
| t | Length of exit port | 0.3 mm |
| a | Height of inlet port | 1.1 mm |
| b | Width of inlet port | 0.5 mm |
| $\alpha$ | Taper angle of inlet conduit | 9°, then 2° |

Figure 3:
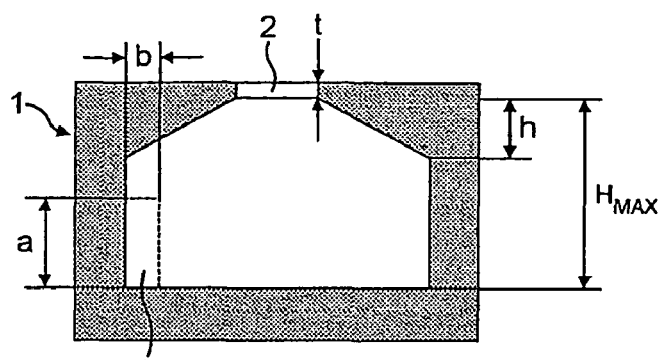
FIG. 3 is a sectional view of a vortex chamber in accordance with the invention.
Figure 4:
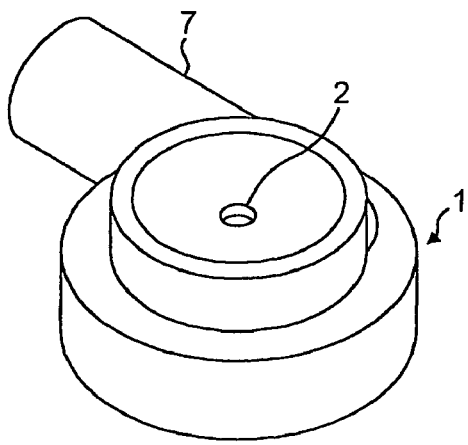
FIG. 4 is a perspective view of a vortex chamber according to an embodiment of the invention.
Figure 5:
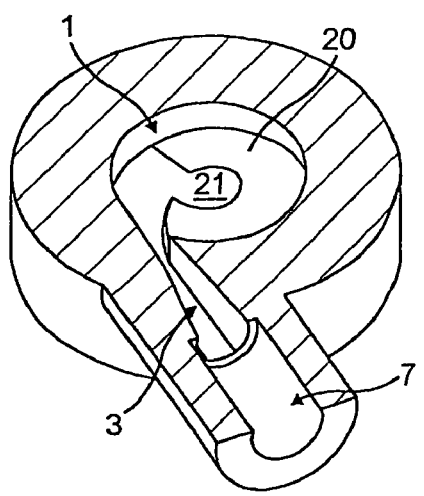
FIG. 5 is a sectional view of the vortex chamber of FIG. 4.
Figure 6:
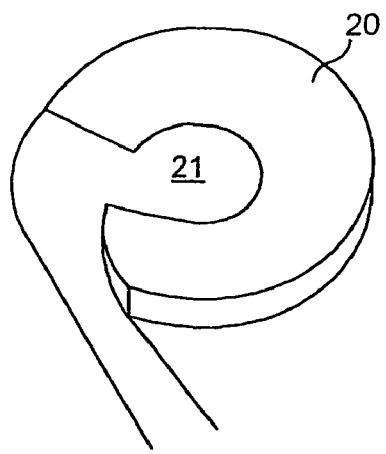
FIG. 6 is a perspective view of a detail of the vortex chamber of FIGS. 4 and 5.

FIG. 3 shows the general form of the vortex chamber of the inhaler of FIG. 1. The geometry of the vortex chamber is defined by the dimensions listed in Table 1. The preferred values of these dimension are also listed in Table 1. It should be noted that the preferred value of the height h of the conical part of the chamber is 0 mm, because it has been found that the vortex chamber functions most effectively when the top (roof 16) of the chamber is flat.

The fine particle fraction of the aerosol generated by the vortex chamber 1 according to the invention is improved relative to a circular vortex chamber 1. The fine particle fraction is the number of particles of medicament emitted in the aerosol having an effective particle diameter of less than 6.8 microns expressed as a proportion of the total initial dose. However, the proportion of the initial dose deposited in the vortex chamber (deposition) is halved, as shown in Table 2.

TABLE 2

Improved performance due to vortex chamber shape.

| Chamber shape | Fine particle fraction | Deposition |
|---|---|---|
| Circular | 68.3% | 13.0% |
| Scroll | 76.1% | 6.5% |

FIGS. 4 to 7 show a further embodiment of the invention in which the vortex chamber 1 includes a ramp 20 which reduces the height of the vortex chamber 1 from the bottom up with increasing angular displacement $\theta$ from the inlet port 3. A substantially circular region 21 in the centre of the vortex chamber 1 remains flat.

Figure 9:
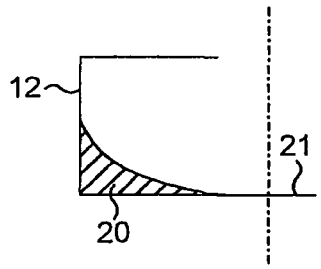
FIGS. 9 to 11 show variations of the interface between the wall and the base of a vortex chamber according to the invention.
Figure 10:
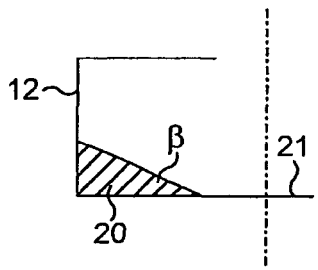
Figure 11:
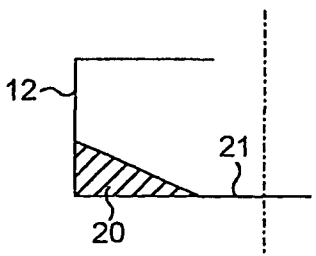

Various options for the cross-section of the ramp are shown in FIGS. 9 to 11. As shown in FIG. 9, the cross-section of the ramp 20 may be a curve, such as a conic section. The value of the radius (or radii) of the curve may increase with increasing angular displacement $\theta$ about the axis of the vortex chamber 1.

Preferably, as shown in FIG. 10, the ramp 20 has a triangular cross-section, with an angle $\beta$ between the base and the upper surface of the ramp 20. The angle $\beta$ is a function of the angular displacement $\theta$, such that $\beta=q(\theta-\theta_1)$ where $\theta_1$ and q are constants.

As shown in FIG. 11, the joints between the ramp 20 and the wall 12 of the vortex chamber and the ramp 20 and the base of the vortex chamber 1 are curved, for example with a fillet radius, to prevent unwanted deposition in this region.

Table 3 shows the performance improvement due to the addition of a ramp 20 for a circular vortex chamber 1.

TABLE 3

Improved performance with ramp

| Chamber shape | Fine particle fraction | Deposition |
|---|---|---|
| No ramp | 68.3% | 13.0% |
| With ramp | 67.8% | 6.5% |

The vertical face (normal to the base) of the ramp 20 where the ramp meets the inlet 3 is likely to attract deposition because of the abrupt change in height. However, by arranging the profile of the face (looking axially) to form a smooth entry, as shown in FIG. 7, contiguous with the inner edge of the inlet 3 air travelling from the inlet scours the face and prevents powder build up.

Figure 8:
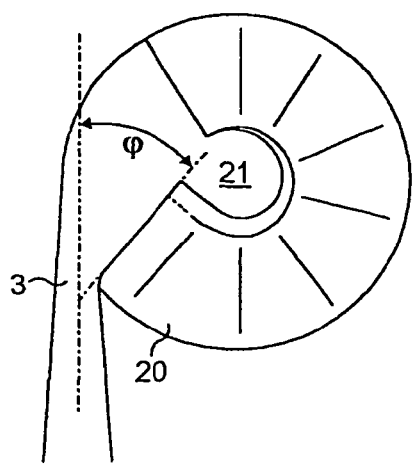
FIG. 8 is a plan view of a variation of the detail of FIG. 7.

In one arrangement the profile is a straight line at 40° (angle $\theta$ in FIG. 8) to the centre line of the inlet, joined to the inlet wall by a tangent curve. This profile follows the pattern of deposition that would be seen in a similar nozzle without a ramp.

Figure 7:
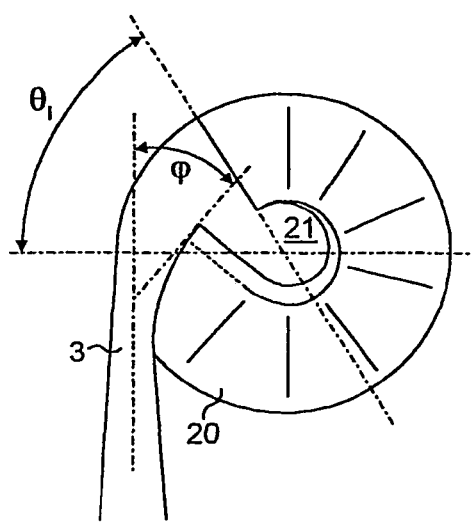
FIG. 7 is a plan view of the detail of FIG. 6.

In a preferred embodiment the profile is a curve moving radially inward as shown in FIG. 7. At one end it joins the inner wall of the inlet tangentially. At the other end it joins a continuation of the inner curve of the ramp at the point where the ramp meets the base.

FIGS. 12 to 15 show various options for the exit port 2 of the vortex chamber 1. The characteristics of the exit plume of the aerosol are determined, at least in part, by the configuration of the exit port 2. For example, if the aerosol leaves an exit port 2 of 1 mm diameter at a flow rate of 2 liters/minute, the velocity at the exit port 2 will be approximately 40 m/s. This velocity can be reduced to a typical inhalation velocity of 2 m/s within a few centimeters of the nozzle by providing a strongly divergent aerosol plume.

Figure 12:
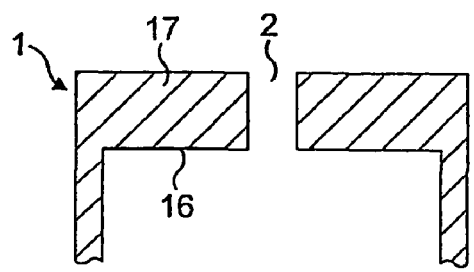
FIGS. 12 to 15 show detail of embodiments of the exit port of the inhaler in accordance with the invention.
Figure 13:
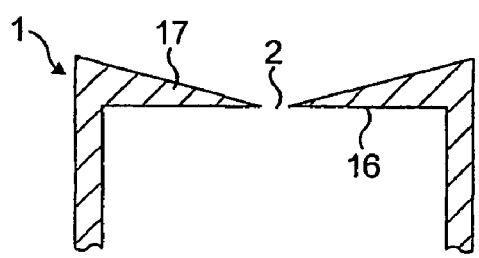

In FIG. 12, the exit port 2 is a simple orifice defined through the upper wall 17 of the vortex chamber 1. However, the thickness of the upper wall 17 means that the exit port 2 has a length which is greater than its diameter. Thus, there is a risk of deposition in the exit port as the aerosol of medicament exits. Furthermore, the tubular exit port tends to reduce the divergence of the exit plume. These problems are solved in the arrangement of FIG. 13 by tapering the upper wall 17 of the vortex chamber 1 towards the exit port 2 so that the exit port 2 is defined by a knife edge of negligible thickness. For an exit port 2 of diameter 1 mm, an exit port length of 2.3 mm gives a plume angle of 60°, whereas reducing this length to 0.3 mm increases the angle to 90°.

Figure 14:
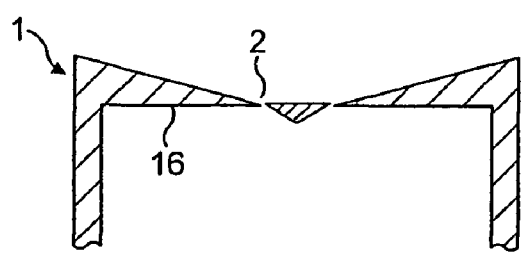
Figure 15:
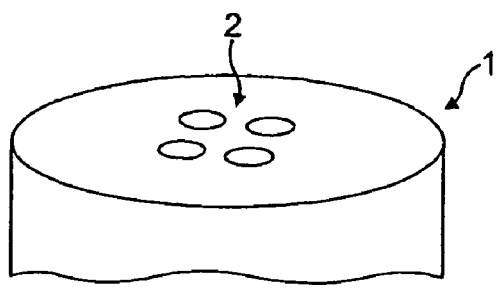

In FIG. 14, the exit port 11 is annular and is also defined by a knife edge. This arrangement produces an exit plume that slows down more quickly than a circular jet, because the annular exit port has a greater perimeter than a circular port of the same diameter and produces a jet that mixes more effectively with the surrounding static air. In FIG. 15, multiple orifices form the exit port 2 and produce a number of smaller plumes which break up and slow down in a shorter distance than a single large plume.

Figure 16:
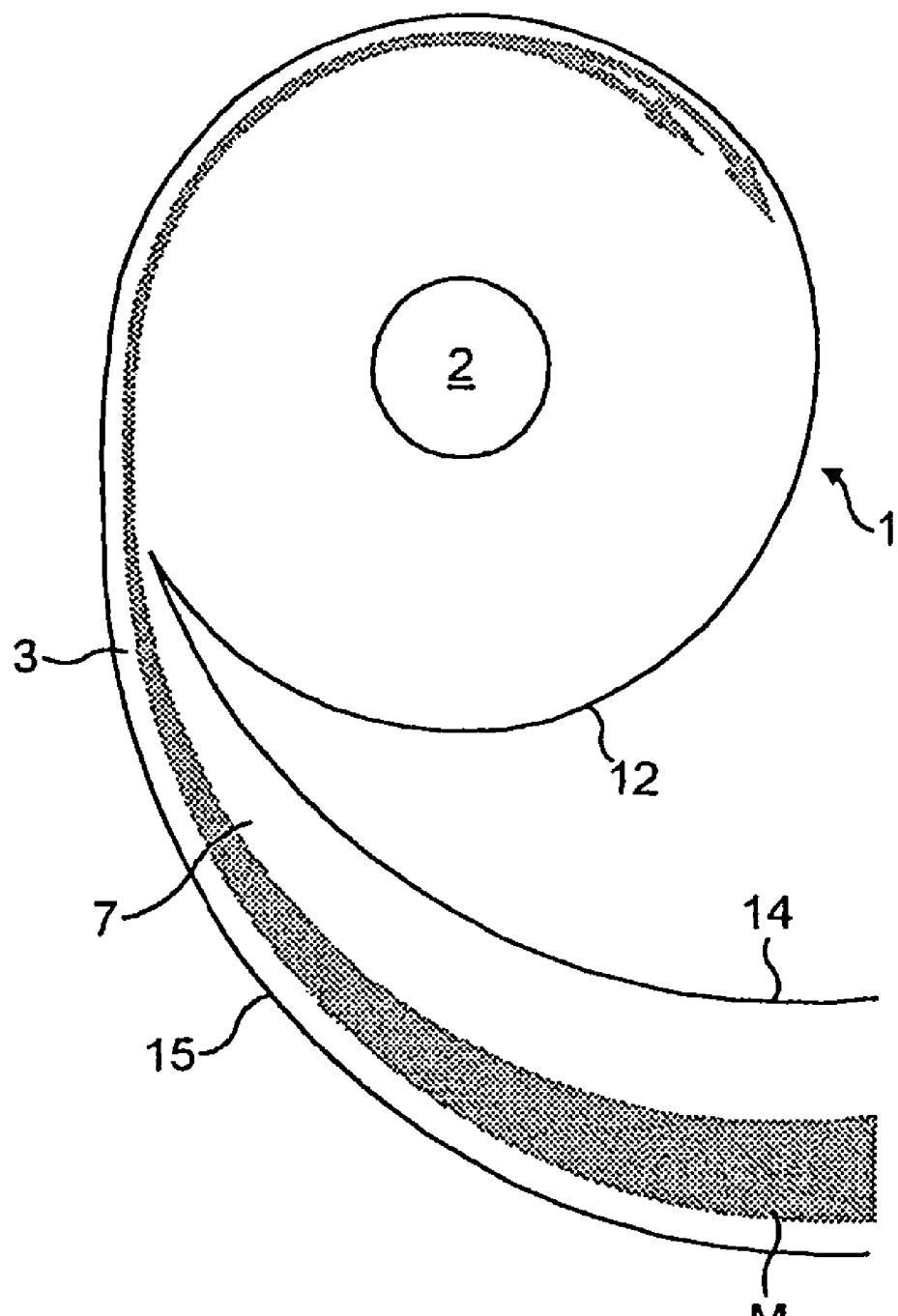
FIG. 16 shows a vortex chamber with an arcuate inlet conduit.

FIG. 16 shows an embodiment of the vortex chamber 1 in which the inlet conduit 7 is arcuate and tapers towards the vortex chamber 1. As shown by the arrows in FIG. 16, the arcuate inlet conduit 7 urges the entrained particles of medicament M towards the outer wall 15 of the inlet conduit 7. In this way, when the medicament enters the vortex chamber 1 through the inlet port 3 the medicament is introduced directly into the boundary layer next to the wall 12 of the vortex chamber 1, where shear forces are at a maximum. In this way, improved deagglomeration is achieved.

The inhaler in accordance with embodiments of the invention is able to generate a relatively slow moving aerosol with a high fine particle fraction. The inhaler is capable of providing complete and repeatable aerosolisation of a measured dose of powdered drug and of delivering the aerosolised dose into the patient's inspiratory flow at a velocity less than or equal to the velocity of the inspiratory flow, thereby reducing deposition by impaction in the patient's mouth. Furthermore, the efficient aerosolising system allows for a simple, small and low cost device, because the energy used to create the aerosol is small. The fluid energy required to create the aerosol can be defined as the integral over time of the pressure multiplied by the flow rate. This is typically less than 5 joules and can be as low as 3 joules.

Although the aerosol of medicament has been described herein as an aerosol of powdered medicament in air, the medicament may be dispersed in any other gas or mixture of gases, as required. Furthermore, although the invention has been described in terms of apparatus, the invention also extends to a method of generating an inhalable aerosol of a powdered medicament as described herein.

In summary, an inhaler for producing inhalable aerosol of a powdered medicament includes an aerosolising device in the form of a vortex chamber. The vortex chamber has a curved wall, a tangential inlet port and an axial exit port. The radius R of the vortex chamber decreases with angular extent from the inlet port. The vortex chamber may include a ramp which reduces the height of the chamber with angular extent. The reduction in effective cross-sectional area of the vortex chamber accelerates the gas flow between the inlet and the outlet to reduce deposition of the medicament.

In the preceding specification, the invention has been described with reference to specific exemplary embodiments thereof. It will, however, be evident that various modifications and changes may be made thereto without departing from the broader spirit and scope of the invention as set forth in the claims that follow. The specification and drawings are accordingly to be regarded in an illustrative manner rather than a restrictive sense.

The invention claimed is:

1. An inhaler for producing an inhalable aerosol of a powdered medicament comprising an aerosolising device in the form of a vortex chamber having an axis and being defined, at least in part, by a wall which forms a curve about the axis, the vortex chamber having a cross-sectional area in a plane bounded by the axis, the plane extending in one direction radially from the axis at a given angular position ($\theta$) about the axis,
wherein the vortex chamber has a substantially tangential inlet port and a substantially axial exit port, and
said cross-sectional area of the vortex chamber decreases with increasing angular position ($\theta$) in the direction, in use, of gas flow between the inlet port and the exit port.

2. An inhaler as claimed in claim 1, wherein the distance (R) of the wall from the axis decreases with angular position ($\theta$).

3. An inhaler as claimed in claim 1, wherein the distance (R) of the wall from the axis decreases with angular position ($\theta$) substantially in accordance with the relationship $R=R_{max}\{1-f(\theta)\}$, where $R_{max}$ is a maximum radius, $f(\theta)$ is a function of ($\theta$), $0 \leq f(\theta) < 1$ for $0 \leq (\theta) < 2\pi$ and $df/d\theta \geq 0$ for $0 < \theta < 2\pi$ and $df/d\theta > 0$ for at least some of the range $0 \leq \theta < 2\pi$.

4. An inhaler as claimed in claim 3, wherein $df/d\theta > 0$ for substantially the whole range $0 \leq \theta < 2\pi$.

5. An inhaler as claimed in claim 3, wherein $df/d\theta$ is a constant (k) for at least some of the range $0 \leq \theta < 2\pi$.

6. An inhaler as claimed in claim 5, wherein $f(\theta)$ is substantially given by $f(\theta)=\theta(k/2\pi)$, where k is a constant and $0 < k < 1$.

7. An inhaler as claimed in claim 5, wherein 5%<k<50%, preferably 10%<k<25%.

8. An inhaler as claimed in claim 7, wherein the interface between the base and the wall is formed by a substantially smooth transition.

9. An inhaler as claimed in claim 1, wherein the vortex chamber is further defined by a base and a roof, and the distance (H) between the base and the roof decreases with angular position ($\theta$).

10. An inhaler as claimed in claim 9, wherein the distance (H) between the base and the roof decreases with angular position ($\theta$) substantially in accordance with the relationship $H=H_{max}\{1-g(\theta)\}$, where H is a maximum height, $g(\theta)$ is a function of $\theta$, $0 \leq g(\theta) < 1$ for $0 \leq \theta < 2\pi$ and $dg/d\theta \geq 0$ for $0 < \theta < 2\pi$ and $dg/d\theta > 0$ for at least some of the range $0 \leq \theta < 2\pi$.

11. An inhaler as claimed in claim 8, wherein $g(\theta)$ is substantially zero for $0 \leq \theta < \theta_1$ where $\theta_1$ is a constant and $dg/d\theta > 0$ for at least some of the range $\theta_1 \leq \theta < 2\pi$.

12. An inhaler as claimed in claim 8, wherein $g(\theta)$ for the range of values of $\theta_1 \leq \theta < \theta_{max}$ is substantially given by $g(\theta)=j(\theta-\theta_1)/(\theta_{max}-\theta_1)$, where j is a constant and $0 < j < 1$.

13. An inhaler as claimed in claim 12, wherein 25%<j<50%, preferably 40%<j<60%.

14. An inhaler as claimed in claim 1, wherein the vortex chamber is further defined by a base, and the distance (d) between the base and a plane which is normal to the axis and is located on the opposite side of the base to the exit part increases with radial position (r) relative to the axis.

15. An inhaler as claimed in claim 14, wherein the distance (d) between the base and the normal plane increases with radial position (r) substantially in accordance with the relationship $d=d_{max}e(r)$, where $d_{max}$ is a maximum distance, $e(r)$ is a function of r, $0 \leq e(r) < 1$ for $0 \leq r \leq R_{max}$ and $de/dr \geq 0$ for $0 \leq r \leq R_{max}$.

16. An inhaler as claimed in claim 15, wherein $e(r)$ is substantially zero for $0 \leq r < r_1$ where $r_1$ is a minimum radius and $de/dr > 0$ for at least some of the range $r_1 \leq r \leq R_{max}$.

17. An inhaler as claimed in claim 15, wherein $e(r)$ for the range of values of $r_1 \leq r \leq R_{max}$ is substantially given by $e(r)=m(r-r_1)/(R_{max}-r_1)$, where m is a constant and $0<m<1$.

18. An inhaler as claimed in claim 1, wherein the vortex chamber is further defined by a base and a roof;

the distance (H) between the base and the roof decreases with angular position (θ); said distance (H) between the base and the roof is given substantially in accordance with the relationship $H=H_{max}\{1-e(r)\}\times\{1-g(\theta)\}$, where H is a maximum height, $g(\theta)$ is a function of θ, $0<g(\theta)<1$ for $0<\theta<2\pi$ and $dg/d\theta>0$ for $0<\theta<2\pi$ and $dg/d\theta>0$ for at least some of the range $0<\theta<2\pi$;

the distance (d) between the base and a plane which is normal to the axis and is located on the opposite side of the base to the exit part increases with radial position (r) relative to the axis;

and wherein distance (d) is given substantially in accordance with the relationship $d=d_{max}e(r)$, where $d_{max}$ is a maximum distance, $e(r)$ is a function of r, $0<e(r)<1$ for $0<r<R_{max}$ and $de/dr>0$ for $0 \leq r \leq R_{max}$.

19. An inhaler as claimed in claim 1, wherein the vortex chamber is further defined by a planar roof and the plane of the roof is substantially normal to the axis.

20. An inhaler as claimed in claim 1, further comprising a pressurized gas source which supplies a gas flow to said inlet port.

21. An inhaler for producing an inhalable aerosol of a powdered medicament comprising an aerosolising device in the form of a vortex chamber having an axis and being defined, at least in part, by a wall which forms a curve about the axis, the vortex chamber having a substantially tangential inlet port and a substantially axial exit port, wherein the vortex chamber is further defined by a base, and the distance (d) between the base and a plane which is normal to the axis and is located on the opposite side of the base to the exit port increases with radial position (r) relative to the axis.

22. An inhaler as claimed in claim 21, wherein the distance (d) between the base and the normal plane increases with radial position (r) substantially in accordance with the relationship $d=d_{max}e(r)$, where $d_{max}$ is a maximum distance, $e(r)$ is a function of r, $0 \leq e(r) < 1$ for $0 \leq r \leq R_{max}$ and $de/dr \geq 0$ for $0 \leq r \leq R_{max}$.

23. An inhaler as claimed in claim 21, wherein the interface between the base and the wall is formed by a substantially smooth transition.

24. An inhaler as claimed in claim 21, further comprising a pressurized gas source which supplies a gas flow to said inlet port.

25. An inhaler for producing an inhalable aerosol of a powdered medicament, the inhaler comprising:

a chamber defined by a top wall, a bottom wall, and a lateral wall, the lateral wall being curved about an axis which intersects the top wall and the bottom wall, the chamber enclosing a cross-sectional area defined by the axis, the top wall, the bottom wall and the lateral wall;

the chamber having an inlet port and an outlet port, the inlet port being tangent to the lateral wall, the outlet port being co-axial with the axis, the cross-sectional area decreasing with increasing angular position from the inlet port in a direction of a gas flow through the inlet port.

26. The inhaler as recited in claim 25, wherein a radius from the axis to the lateral wall decreases with increasing angular position.

27. The inhaler as recited in claim 26, wherein the radius from the axis to the lateral wall decreases with increasing angular position in accordance with a relationship $R=R_{max}\{1-f(\theta)\}$, where R is the radius, θ is the angular position, wherein $R_{max}$ is a maximum radius from the axis to the lateral wall, $f(\theta)$ is a function of θ, $0 \leq f(\theta) < 1$ for $0 \leq \theta < 2\pi$ and $df/d\theta \geq 0$ for $0 < \theta < 2\pi$ and $df/d\theta > 0$ for at least a portion of the range $0 \leq \theta < 2\pi$.

28. The inhaler as recited in claim 27, wherein $df/d\theta > 0$ for substantially all of the range $0 \leq \theta < 2\pi$.

29. The inhaler as recited in claim 27, wherein $df/d\theta$ is a constant (k) for at least a portion of the range $0 \leq \theta < 2\pi$.

30. An inhaler as claimed in claim 29, wherein $f(\theta)$ is substantially given by $f(\theta)=\theta(k/2\pi)$, where k is the constant and $0<k<1$.

31. The inhaler as recited in claim 29, wherein $5\%<k<50\%$.

32. The inhaler as recited in claim 31, wherein $10\%<k<25\%$.

33. The inhaler as recited in claim 25, a distance from the bottom wall and to the top wall decreases with increasing angular position.

34. The inhaler as recited in claim 33, wherein the height decreases with increasing angular position substantially in accordance with a relationship $H=H_{max}\{1-g(\theta)\}$, where H the height, $H_{max}$ is a maximum height, θ is the angular position, $g(\theta)$ is a function of θ, $0 \leq g(\theta) < 1$ for $0 \leq \theta < 2\pi$ and $dg/d\theta \geq 0$ for $0 < \theta < 2\pi$ and $dg/d\theta > 0$ for at least a portion of the range $0 \leq \theta < 2\pi$.

35. The inhaler as recited in claim 34, wherein $g(\theta)$ is substantially zero for $0 \leq \theta < \theta_1$ where $\theta_1$ is a constant and $dg/d\theta > 0$ for at least a portion of the range $\theta_1 \leq \theta < 2\pi$.

36. The inhaler as recited in claim 34, wherein $g(\theta)$ for a range of values of $\theta_1 \leq \theta < \theta_{max}$ is substantially given by $g(\theta)=j(\theta-\theta_1)/(\theta_{max}-\theta_1)$, where j is a constant and $0<j<1$.

37. The inhaler as recited in claim 36, wherein $25\%<j<50\%$.

38. The inhaler as recited in claim 37, wherein $40\%<j<60\%$.

39. The inhaler as recited in claim 34, wherein the height between the base and the roof is given substantially by $H=H_{max}\{1-e(r)\}\times\{1-g(\theta)\}$.

40. An inhaler as claimed in claim 25, further comprising a pressurized gas source which supplies a gas flow to said inlet port.

41. An inhaler for producing an inhalable aerosol of a powdered medicament, the inhaler comprising: a chamber including a wall, a base, an inlet port and an exit port, the chamber having an axis that is co-axial with the exit port and intersects the base, the wall being curved about the base, the inlet port being tangential to the wall, a height between the base and a plane normal to the axis at the exit port decreasing as a radial position from the axis to the inlet port increases.

42. A method of inhaling an aerosol of a powdered medicament, the method comprising:

generating an air flow through an inlet port of a chamber;

directing the air flow through the chamber, the chamber having an axis and a wall curved about the axis, the air flow rotating about the axis; and directing the air flow through an exit port of the chamber, wherein a direction of the air flow through the inlet port is tangential to the wall, and a direction of the air flow through the exit port is parallel to the axis, and wherein a cross-sectional area of the air flow through the chamber is in a plane normal to the air flow and decreases with increasing distance from the inlet port.

43. The method of claim 42, further comprising supplying an air flow to said inlet port via a pressurized gas source.

* * * * *